US00PP25364P2

(12) United States Plant Patent
Hoogenraad et al.

(10) Patent No.: US PP25,364 P2
(45) Date of Patent: Mar. 24, 2015

(54) ***BERBERIS* PLANT NAMED 'HOHO 1'**

(50) Latin Name: *Berberis thungergii*
Varietal Denomination: Hoho 1

(71) Applicants: Mark Sebastiaan Hoogenraad, Ederveen (NL); Ralph Matheus Hoof, Zevenaar (NL)

(72) Inventors: Mark Sebastiaan Hoogenraad, Ederveen (NL); Ralph Matheus Hoof, Zevenaar (NL)

( * ) Notice: Subject to any disclaimer, the term of this patent is extended or adjusted under 35 U.S.C. 154(b) by 48 days.

(21) Appl. No.: 13/986,429

(22) Filed: May 1, 2013

(51) Int. Cl.
*A01H 5/00* (2006.01)

(52) U.S. Cl.
USPC ..... Plt./241

(58) Field of Classification Search
CPC ..... A01H 5/12; A01H 5/00
USPC ..... Plt./241
See application file for complete search history.

*Primary Examiner* — June Hwu
*Assistant Examiner* — Keith Robinson
(74) *Attorney, Agent, or Firm* — Penny J. Aguirre

(57) ABSTRACT

A new cultivar of *Berberis*, 'Hoho 1', that is characterized by its compact plant habit, its moderate growth habit, its young shoots that are deep pink-red in color and its mature foliage that is heavily mottled with pink and red.

2 Drawing Sheets

Botanical classification: *Berberis thungergii*.
Cultivar designation: 'Hoho 1'.

BACKGROUND OF THE INVENTION

The present invention relates to a new and distinct cultivar of *Berberis thungerii*, and will be referred to hereafter by its cultivar name, 'Hoho 1'. 'Hoho 1' is grown for use as a landscape shrub.

The new cultivar was discovered by the Inventors as a chance seedling in a production field in June of 2011 in Zevenaar, The Netherlands. The parent plant is believed to be 'Rose Glow' (not patented) as the field contained propagation stock plants of 'Rose Glow'.

Asexual propagation of the new cultivar was first accomplished by one the Inventors using softwood stem cuttings in Zevenaar, The Netherlands in June of 2011. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar, which in combination distinguish 'Hoho 1' as a new and distinct cultivar of *Berberis*.

1. 'Hoho 1' exhibits a compact plant habit.
2. 'Hoho 1' exhibits a moderate growth habit.
3. 'Hoho 1' exhibits young shoots that are deep pink-red in color.
4. 'Hoho 1' exhibits mature foliage that is heavily mottled with pink and red.

The probable parent, 'Rose Glow', differs from 'Hoho 1' in having a less compact plant habit and faster growth rate, less mottled foliage, and young shoots that are lighter pink-red in color. 'Hoho 1' can be most compared to the cultivars 'Harlequin' (not patented) and 'Rosy Rocket' (U.S. Plant Pat. No. 18,413). Both cultivars are similar to 'Hoho 1' in having foliage that is mottled with pink and red. 'Harlequin' differs from 'Hoho 1' in having a more vigorous growth habit, young shoots that are less deeply colored, and foliage with less intense mottling. 'Rosy Rocket' differs from 'Hoho 1' in having a columnar plant habit, young shoots that are less deeply colored, and foliage with less intense mottling.

BRIEF DESCRIPTION OF THE DRAWINGS

The accompanying colored photographs illustrate the overall appearance and distinct characteristics of the new *Berberis*. The photographs were taken of a plant two-years in age as grown outdoors in a 2-liter container in Zevenaar, The Netherlands.

The photograph in FIG. 1 provides a side view of 'Hoho 1'.

Figure 1:
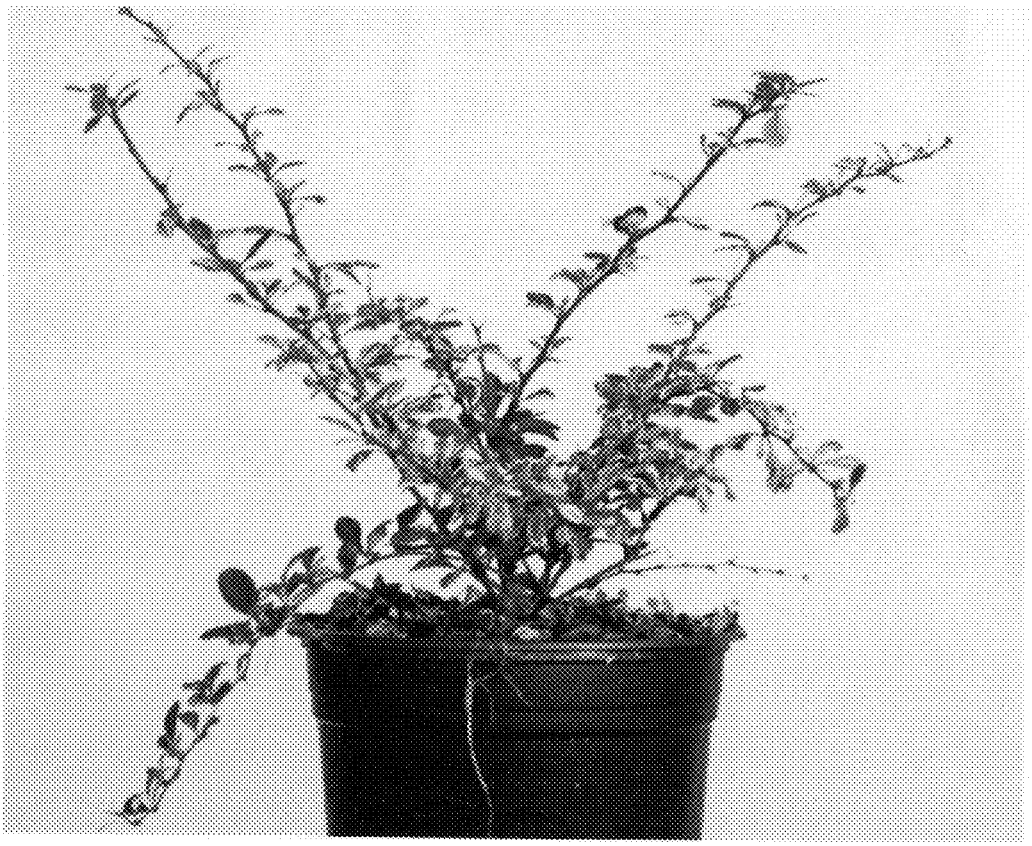
Figure 2:
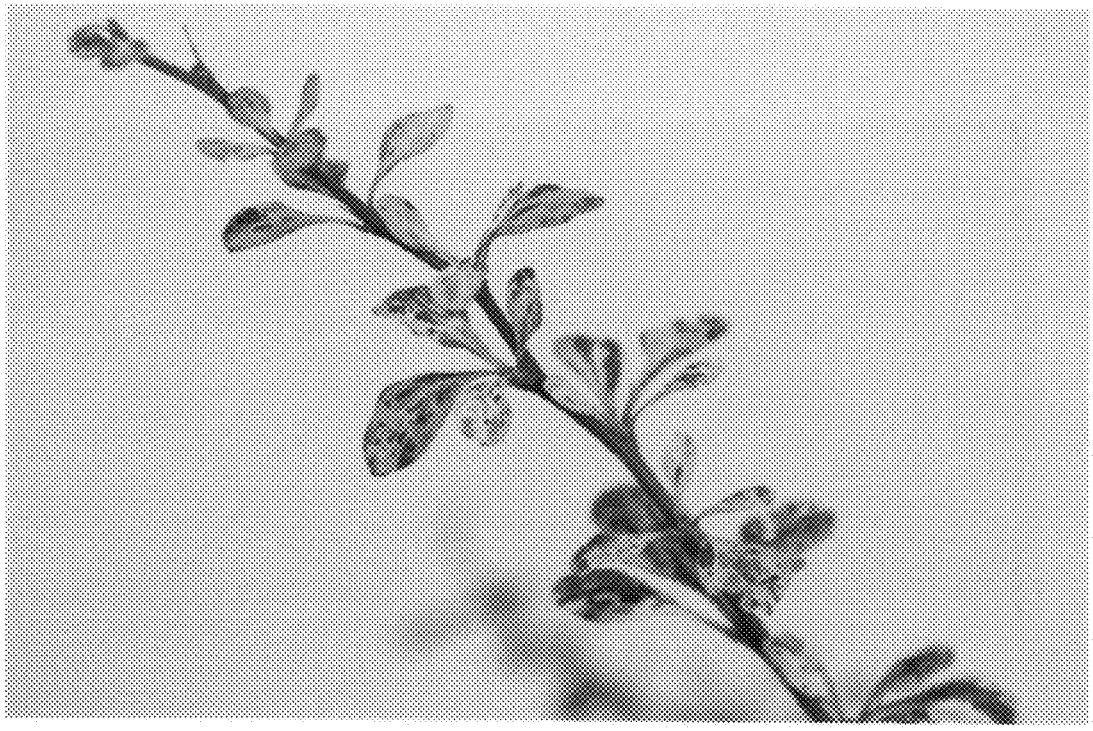

The photograph in FIG. 2 provides a view of the new shoots of 'Hoho 1'.

Figure 3:
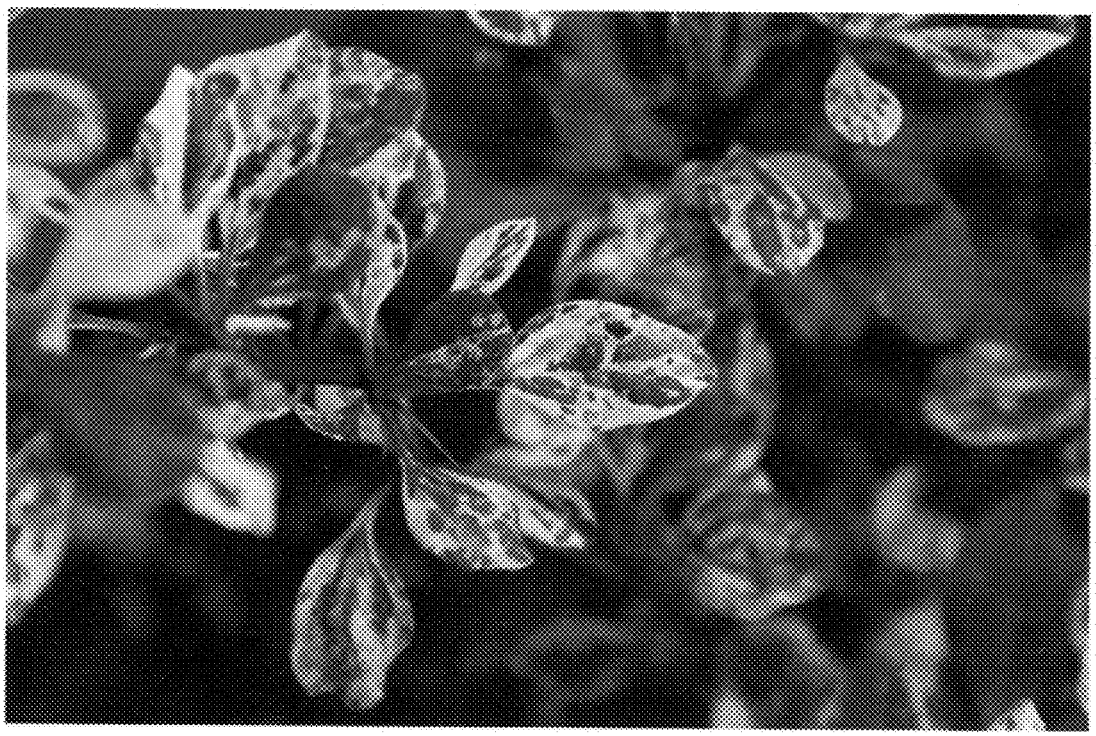

The photograph in FIG. 3 provides a close-up view of the foliage of 'Hoho 1'.

The colors in the photographs may differ slightly from the color values cited in the detailed botanical description, which accurately describe the colors of the new *Berberis*.

DETAILED BOTANICAL DESCRIPTION OF THE PLANT

The following is a detailed description of two-year-old plants of the new cultivar field grown outdoors in 2-liter containers in Zevenaar, The Netherlands. Plants were grown under average day temperatures of 10° to 23° C. and average night temperatures of 1° to 14° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type.*—Deciduous shrub.

*Plant habit.*—Compact, upright spreading.

*Height and spread.*—Reaches about 23.1 cm in height and 34.5 cm in spread in a 2-liter container and matures to 150 cm in height and 100 cm to spread.

*Cold hardiness.*—At least in U.S.D.A. Zone 5.

*Disease and pest resistance.*—No susceptibility or resistance to diseases or pests has been observed, however the foliage has been observed to be healthy under the conditions tested and no infections by wheat yellow rust caused by *Puccinia striiformis* has been observed.

*Root description.*—Fibrous, 162C in color with blotches of 163A.

*Growth rate.*—Moderate, about 15 cm in one season on a young plant.

*Propagation.*—Softwood cuttings.

Stem description:

*Stem size.*—Lateral branches are an average of 17 cm in length and 1.3 cm in diameter.

*Stem shape.*—Round.

*Stem color.*—Young shoots; 187A, mature stems; a blend of 200C and 200D.

*Stem surface.*—Slightly glossy.

*Stem strength.*—Strong.

*Internode length.*—Average of 1.3 cm.

*Branching habit.*—Moderate to high with an average of 11 lateral branches.

*Branching aspect.*—Lateral branches slightly angled, in an average angle of 55°.

Foliage description:

*Leaf shape.*—Obovate.

*Leaf division.*—Simple.

*Leaf base.*—Long attenuate.

*Leaf apex.*—Obtuse to broadly acute.

*Leaf margins.*—Entire.

*Leaf attachment.*—Sessile.

*Leaf arrangement.*—Alternate, clustered.

*Leaf surface.*—Both sides are smooth and dull.

*Leaf color.*—Upper surface immature foliage; N200D to 200A, heavily marbled 50A, lower surface immature foliage; N187C to N187D, heavily marbled 51B, mature foliage upper surface; marbled colors ranging between 147A and N200A to N200B, and heavily marbled 48C to 48D, older shaded leaves at base of branch ("inside" the plant in the shade) 200A and N200A, tinged 147A, mature lower surface foliage; between 147A and 147D, heavily marbled 49B to 49C, older shaded leaves at base of branch ("inside" the plant in the shade) between 147B and 148B.

*Leaf number.*—5 per cluster at each node, average of 14 nodes per lateral branch, average of 70 leaves per lateral branch.

*Leaf size.*—Average of 2.2 cm in length and 1.2 cm in width.

*Leaf aspect.*—Held upward at about a 45° angle.

*Leaf fragrance.*—None.

*Leaf veins.*—Pinnate, upper surface color; same as upper leaf color, lower surface color; 144A to 144B.

*Petioles.*—Average of 5 mm in length and 1 mm in width, 185B in color, glabrous surface.

*Thorn.*—Below each node is an average of one (occasionally two) very sharp thorns; average of 10 mm length, average width at base is 1 mm, color; young thorns are 179C to 179D, mid-section is 162C, tip is N199B, 151C to 151D in color and 200A at tip, older thorns are 100B, mid-section is N199C to N199D.

Flower description:

*Flowering.*—No flowers have been observed.

Fruit and seed: Seed production has not been observed.

It is claimed:

1. A new and distinct cultivar of *Berberis* plant named 'Hoho 1' as herein illustrated and described.

* * * * *